United States Patent
Li et al.

(10) Patent No.: US 10,512,435 B2
(45) Date of Patent: *Dec. 24, 2019

(54) SYSTEMS FOR MAPPING LOCAL CONDUCTION VELOCITY

(71) Applicant: St. Jude Medical, Cardiology Division, Inc., St. Paul, MN (US)

(72) Inventors: Wenwen Li, San Jose, CA (US); Erhan Erdemir, Maplewood, MN (US); Eric J. Voth, Maplewood, MN (US); Valtino X. Afonso, Oakdale, MN (US); Carlo Pappone, Cernusco Lombardone (IT)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/817,023

(22) Filed: Nov. 17, 2017

(65) Prior Publication Data

US 2018/0116608 A1    May 3, 2018

Related U.S. Application Data

(63) Continuation of application No. 15/278,092, filed on Sep. 28, 2016, now Pat. No. 9,872,653, which is a
(Continued)

(51) Int. Cl.
*A61B 5/0402* (2006.01)
*A61B 5/00* (2006.01)
(Continued)

(52) U.S. Cl.
CPC ......... *A61B 5/7278* (2013.01); *A61B 5/0422* (2013.01); *A61B 5/0452* (2013.01);
(Continued)

(58) Field of Classification Search
None
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| CN | 101292870 | 10/2008 |
| CN | 101675879 | 3/2010 |

(Continued)

OTHER PUBLICATIONS

Barnette et al., Estimation of 3-D Conduction Velocity Vector Fields from Cardiac Mapping Data, IEEE Biomedical Engineering, vol. 47, No. 8, pp. 1027-1035, Aug. 2000.
(Continued)

*Primary Examiner* — Kennedy Schaetzle
(74) *Attorney, Agent, or Firm* — Wiley Rein LLP

(57) ABSTRACT

The local conduction velocity of a cardiac activation wavefront can be computed by collecting a plurality of electrophysiology ("EP") data points using a multi-electrode catheter, with each EP data point including both position data and local activation time ("LAT") data. For any EP data point, a neighborhood of EP data points, including the selected EP data point and at least two additional EP data points, can be defined. Planes of position and LATs can then be defined using the positions and LATs, respectively, of the EP data points within the neighborhood. A conduction velocity can be computed from an intersection of the planes of positions and LATs. The resultant plurality of conduction velocities can be output as a graphical representation (e.g.,
(Continued)

an electrophysiology map), for example by displaying vector icons arranged in a uniform grid over a three-dimensional cardiac model.

8 Claims, 5 Drawing Sheets

Related U.S. Application Data continuation of application No. 14/884,534, filed on Oct. 15, 2015, now Pat. No. 9,474,491.

(60) Provisional application No. 62/063,987, filed on Oct. 15, 2014.

(51) Int. Cl.
*A61B 5/042* (2006.01)
*A61B 5/0452* (2006.01)
*A61B 5/053* (2006.01)

(52) U.S. Cl.
CPC .......... *A61B 5/0538* (2013.01); *A61B 5/6852* (2013.01); *A61B 5/743* (2013.01); *A61B 5/7264* (2013.01); *A61B 5/7282* (2013.01); *A61B 2505/05* (2013.01); *A61B 2562/04* (2013.01)

(56) References Cited

U.S. PATENT DOCUMENTS

| | | |
|---|---|---|
| 6,187,032 B1 | 2/2001 | Ohyu et al. |
| 6,301,496 B1 | 10/2001 | Reisfeld |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 8,768,440 B1 | 7/2014 | Brodnick et al. |
| 9,050,011 B2 | 6/2015 | Rubinstein et al. |
| 9,271,680 B2 | 3/2016 | Dubois et al. |
| 9,474,491 B2 * | 10/2016 | Li ........................ A61B 5/0538 |
| 9,610,023 B2 | 4/2017 | Dubois et al. |
| 9,872,653 B2 * | 1/2018 | Li ........................ A61B 5/0538 |
| 2002/0055674 A1 | 5/2002 | Ben-Haim et al. |
| 2008/0194979 A1 | 8/2008 | Madry et al. |
| 2011/0251505 A1 | 10/2011 | Narayan et al. |
| 2016/0089048 A1 | 3/2016 | Brodnick et al. |

FOREIGN PATENT DOCUMENTS

| | | |
|---|---|---|
| CN | 103479346 | 1/2014 |
| CN | 103565432 | 2/2014 |
| EP | 1070480 | 1/2001 |
| JP | 2014-506171 | 3/2014 |
| JP | 2014-124533 | 7/2014 |
| WO | 2012/092016 | 7/2012 |

OTHER PUBLICATIONS

Bayly et al., Estimation of Conduction Velocity Vector Fields from Epicardial Mapping Data, IEEE Transactions on Biomedical Engineering, vol. 45, No. 5, pp. 563-571, May 1998.

Berens, CircStat: A MATLAB Toolbox for Circular Statistics, Journal of Statistical Software, vol. 31, issue 10, pp. 1-21, Sep. 2009.

Mase et al., Automatic Reconstruction of Activation and Velocity Maps from Electro-Anatomic Data by Radial Basis Functions, 32nd Annual International Conference of the IEEE EMBS, pp. 2608-2611, Aug. 31-Sep. 4, 2010.

\* cited by examiner

SYSTEMS FOR MAPPING LOCAL CONDUCTION VELOCITY

CROSS-REFERENCE TO RELATED APPLICATIONS

This application is a continuation of U.S. application Ser. No. 15/278,092, filed 28 Sep. 2016 (the '092 application), now U.S. Pat. No. 9,872,653, which is a continuation of U.S. application Ser. No. 14/884,534, filed 15 Oct. 2015 (the '534 application), now U.S. Pat. No. 9,474,491, which in turn claims the benefit of and priority to U.S. application No. 62/063,987, filed 15 Oct. 2014 (the '987 application). The '092 application, '534 application, and '987 application are each hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for computing local conduction velocities from data collected by an electrophysiology probe (e.g., a contact or non-contact mapping catheter).

Two mainstay hypotheses of arrhythmia maintenance mechanisms are single source focus and circus movement reentry. To study both mechanisms and identify the conduction circuits that sustain the arrhythmia, it is desirable to map both activation direction and activation speed during the arrhythmia.

It is known to use an isochrone map based on local activation time ("LAT") to map the propagation of a cardiac activation wavefront. To produce such a map, however, there must be a common activation time reference, which is normally a stable cardiac detection. Thus, isochronal maps of LATs are typically limited to cardiac-triggered maps.

BRIEF SUMMARY

Disclosed herein is a method of computing local conduction velocity of a cardiac activation wavefront, including: collecting a plurality of electrophysiology ("EP") data points using a multi-electrode catheter, each EP data point of the plurality of EP data points including position data and local activation time ("LAT") data; selecting an EP data point from the plurality of EP data points; defining a neighborhood of EP data points including the selected EP data point and at least two additional EP data points from the plurality of EP data points; defining a plane of positions using the positions of the EP data points within the neighborhood of EP data points; defining a plane of LATs using the LATs of the EP data points within the neighborhood of EP data points; and computing a conduction velocity for the selected EP data point from an intersection of the plane of positions and the plane of LATs if the plane of positions and the plane of LATs intersect. These steps can be repeated for a plurality of EP data points, thereby computing a plurality of conduction velocities. These plurality of conduction velocities can then be output as a three-dimensional graphical representation, such as by using a plurality of conduction velocity vector icons arranged in a uniform grid over a three-dimensional model of at least a portion of a heart.

In certain aspects, the LATs for the plurality of EP data points are computed relative to activation at a stable reference electrode. In other aspects, they are computed relative to activation at an electrode carried by the multi-electrode catheter.

The step of computing a conduction velocity for the selected EP data point from an intersection of the plane of positions and the plane of LATs can include: computing a plurality of conduction velocity constituents for the selected EP data point, each of the plurality of conduction velocity constituents corresponding to a conduction velocity during one of a plurality of activation windows of a time segment; and computing a composite conduction velocity over the time segment for the selected EP data point from the plurality of conduction velocity constituents. Computing a plurality of conduction velocity constituents for the selected EP data point can, in turn, include: selecting an electrode carried by the multi-electrode catheter as a reference electrode, the reference electrode having an associated reference electrophysiological signal; detecting a plurality of activations within the reference electrophysiological signal; defining a plurality of activation windows, wherein each of the plurality of activation windows contains one of the detected plurality of activations; and, for each of the plurality of activation windows: defining the plane of positions and the plane of LATs for the selected EP data point; and computing the conduction velocity constituent for the selected EP data point from the intersection of the plane of positions and the plane of LATs for the selected EP data point, thereby computing the plurality of conduction velocity constituents for the selected EP data point.

According to embodiments disclosed herein, the electrode carried by the multi-electrode catheter that is selected as a reference electrode can be the electrode having a greatest number of activations within the time segment as the reference electrode.

It is contemplated that the composite conduction velocity over the time segment can be computed as the mean of the plurality of conduction velocity constituents. Alternatively, the composite conduction velocity over the time segment can be a dominant conduction velocity selected or computed from the plurality of conduction velocity constituents.

In other embodiments, a conduction velocity consistency index indicating a degree of consistency in a direction of the conduction velocity constituents for a selected EP data point can be computed. The conduction velocity consistency index can include a ratio of an absolute magnitude of the composite conduction velocity and an average absolute magnitude of the conduction velocity constituents, a ratio of an absolute magnitude of the composite conduction velocity and an absolute magnitude of an average of the conduction velocity constituents, an average normalized dot product of the conduction velocity constituents and the composite conduction velocity, and/or a weighting factor. The weighting factor can account for the number of activation windows for which a valid conduction velocity constituent was computed (e.g., those activation windows where the plane of positions and the plane of LATs intersected).

The plane of positions can be defined from a least squares fit of the positions of the EP data points in the neighborhood of EP data points. Similarly, the plane of LATs can be defined from a least squares fit of the positions of pseudo-EP data points, the coordinates of which can be defined by a position of the corresponding EP data point within the plane of positions and the LAT for the corresponding data point.

Also disclosed herein is a system for computing local conduction velocity of a cardiac activation wavefront, including: a conduction velocity processor configured to receive as input a plurality of electrophysiology ("EP") data points collected using a multi-electrode catheter, each EP data point of the plurality of EP data points having a position and a local activation time ("LAT"), and, for a selected EP data point of the plurality of EP data points: define a neighborhood of EP data points including the selected EP data point and at least two additional EP data points from the plurality of EP data points; define a plane of positions using the positions of the EP data points within the neighborhood of EP data points; define a plane of LATs using the LATs of the EP data points within the neighborhood of EP data points; and compute a conduction velocity from an intersection of the plane of positions and the plane of LATs, if the plane of positions and the plane of LATs intersect; and a mapping processor configured to generate a three-dimensional graphical representation of a plurality of conduction velocities computed by the conduction velocity processor.

In yet another aspect, a method of computing local conduction velocity of a cardiac activation wavefront from a plurality of electrophysiology ("EP") data points includes: selecting an EP data point from the plurality of EP data points; defining a neighborhood of EP data points including the selected EP data point and at least two additional EP data points from the plurality of EP data points; defining a plane of positions using the positions of the EP data points within the neighborhood of EP data points; defining a plane of LATs using the LATs of the EP data points within the neighborhood of EP data points; and computing a conduction velocity for the selected EP data point from an intersection of the plane of positions and the plane of LATs if the plane of positions and the plane of LATs intersect.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses, and systems for the creation of electrophysiology maps (e.g., electrocardiographic maps) that provide information regarding the local conduction velocity of a cardiac activation wavefront. Advantageously, because local conduction velocity is reference-independent, the teachings herein can be applied to compute local conduction velocity for both regular activations (including both sinus rhythm and regular cardiac arrhythmias) and irregular activations (such as irregular arrhythmias, including atrial fibrillation), where a stable reference may not be available.

Figure 1:
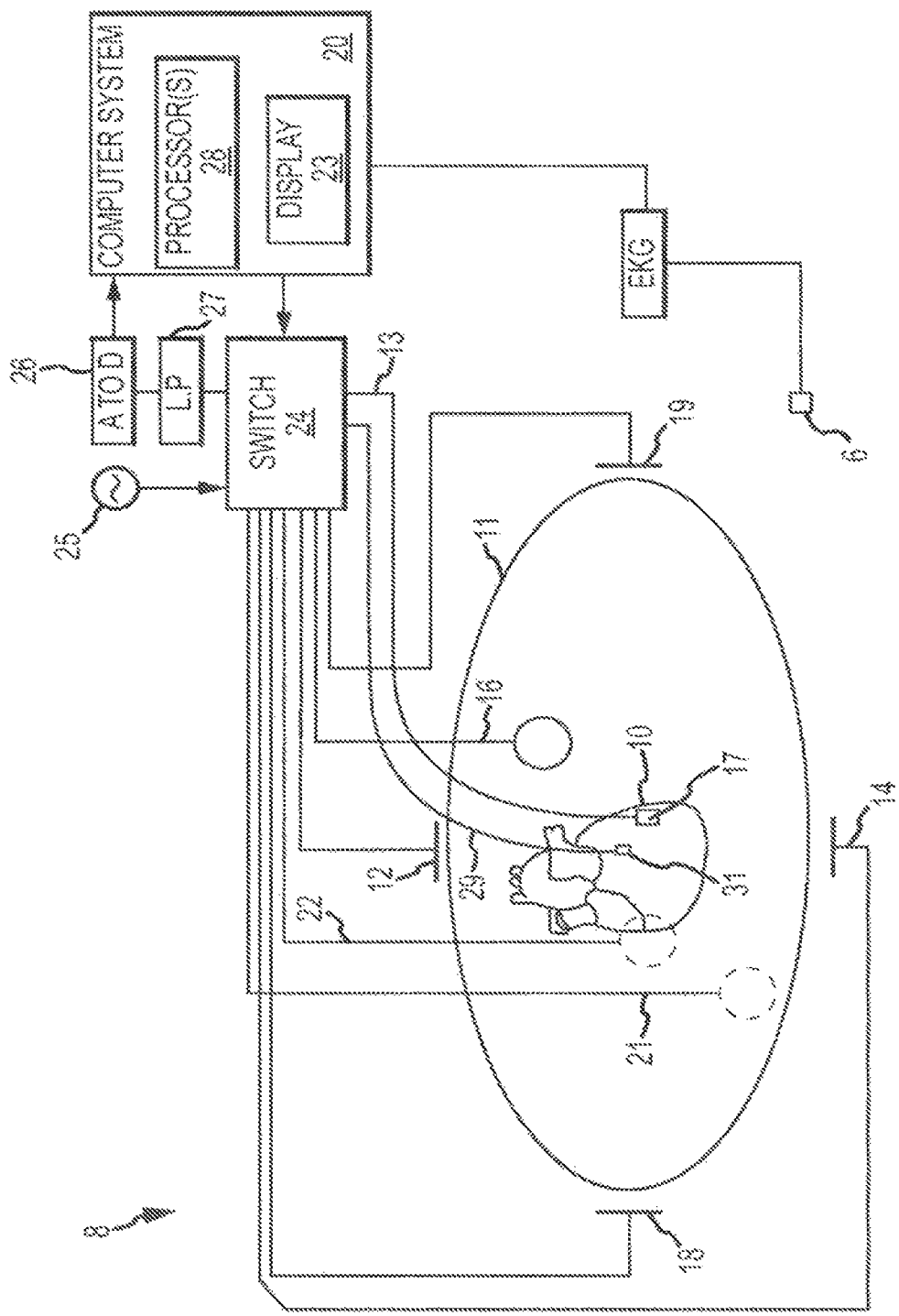
FIG. 1 is a schematic of an electrophysiology system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data, including, but not limited to, local activation time ("LAT"), at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
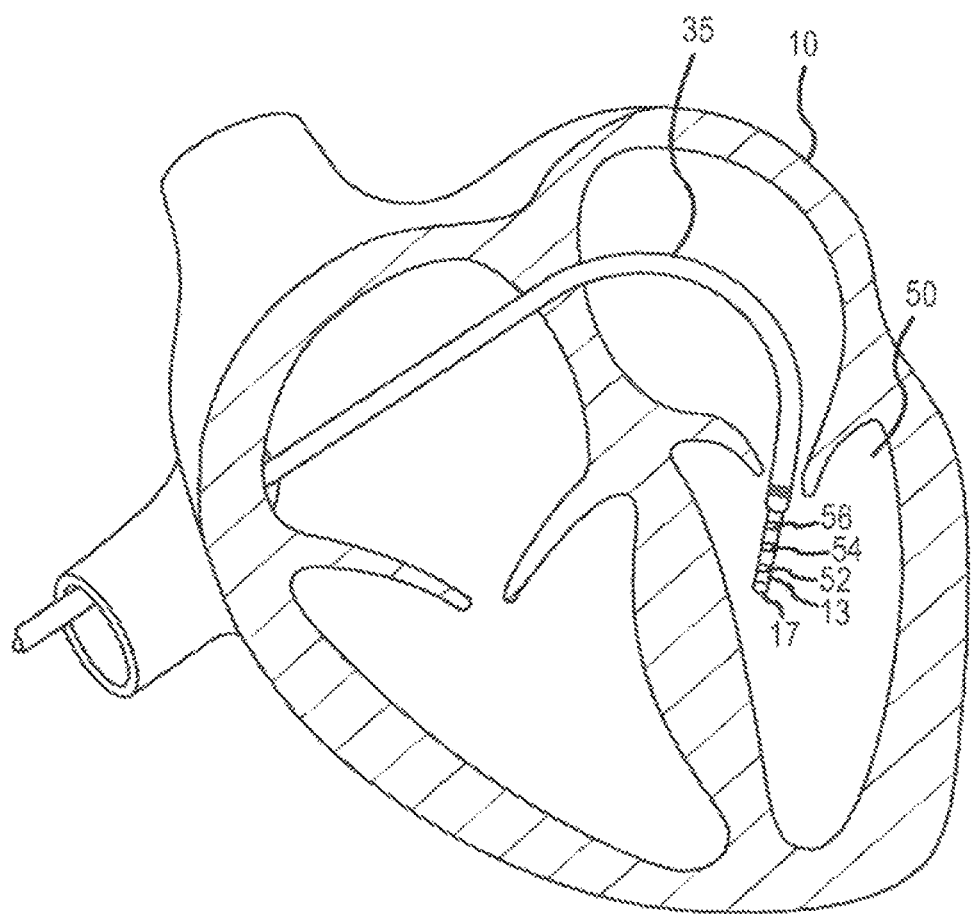
FIG. 2 depicts an exemplary multi-electrode catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the conduction velocity mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the maps disclosed herein.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

One basic methodology of computing local conduction velocity will be explained with reference to the flowchart of representative steps presented as FIG. 3. In some embodiments, for example, the flowchart may represent several exemplary steps that can be carried out by the computer 20 of FIG. 1 (e.g., by one or more processors 28) to generate a conduction map such as described herein. It should be understood that the representative steps described below can be either hardware- or software-implemented. For the sake of explanation, the term "signal processor" is used herein to describe both hardware- and software-based implementations of the teachings herein.

In step 302, a plurality of electrophysiology ("EP") data points are collected, for example using a multi-electrode catheter 13 as described above. As will be familiar to the person of ordinary skill in the art, and as described above, each EP data point will include location information and EP information, including, without limitation, LAT information.

In block 304, one of the EP data points is selected for computation of local conduction velocity. Then, in block 306, a neighborhood of EP data points, including the EP data point selected in block 304 and at least two additional data points, is defined. The size of the neighborhood of EP data points can be user selected based, for example, upon the spatial density of the electrodes carried by multi-electrode catheter 13. That is, as electrode density increases, the user can decrease the size of the neighborhood of EP data points. Alternatively, and in other embodiments, the neighborhood of EP data points can be selected automatically via criteria pre-programmed within the computer system 20 and/or provided by another component.

In blocks 308 and 310, two different planes are computed from the neighborhood of EP data points. In block 308, a plane of positions is computed using the positions of the EP data points within the neighborhood. For example, the plane of positions can be computed from a least squares fit of the positions of the EP data points within the neighborhood of EP data points.

Similarly, in block 310, a plane of LATs is computed using the positions of the EP data points within the neighborhood. For example, in one aspect, a new pseudo-EP data point is defined for each of the EP data points within the neighborhood. For each pseudo-EP data point, two of the coordinates are determined by the in-plane position of the EP data point, such as computed when computing the plane of positions. The third coordinate, which can be normal to the plane of positions, can be the value of the LAT for the EP data point. The plane of LATs can be computed from a least squares fit of the positions of the pseudo-EP data points.

Block 312 checks whether the plane of positions and the plane of LATs intersect. If they do not intersect, then in block 314, the local conduction velocity for the selected EP data point is set to "undefined." If, however, the two planes do intersect, then the intersection of planes is used to compute the local conduction velocity (i.e., magnitude and direction) at the selected EP data point in block 316. In some embodiments, the direction of the local conduction velocity is normal to the line of intersection between the plane of positions and the plane of LATs, while the magnitude of the local conduction velocity can be computed as the cotangent of the angle between the plane of positions and the plane of LATs.

The process can then repeat from the selection of an EP data point in block 304 to compute a plurality of local conduction velocities for as many as all of the EP data points collected in block 302.

Figure 4:
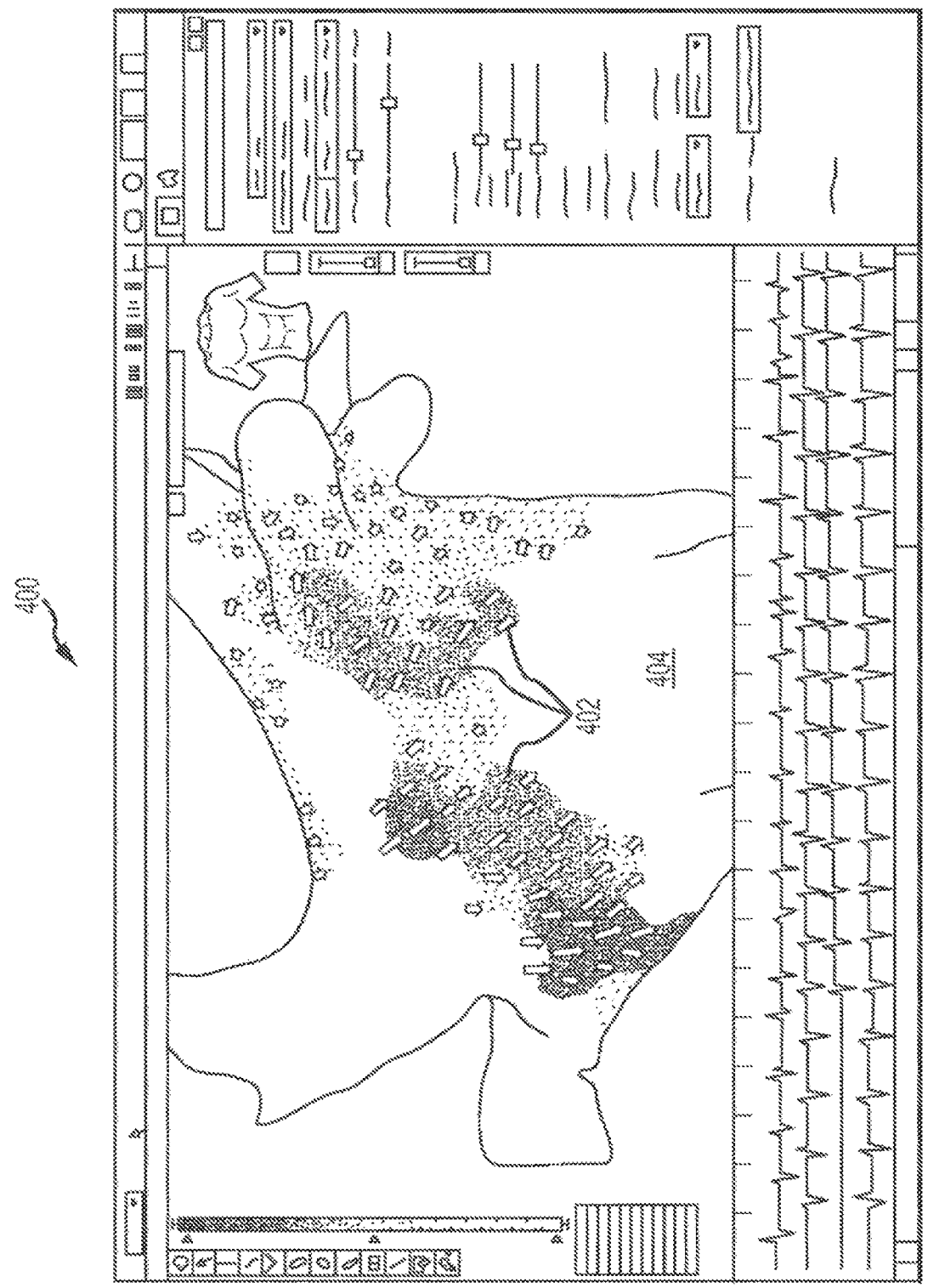
FIG. 4 is an exemplary conduction velocity map according to an embodiment disclosed herein.

Once a plurality of local conduction velocities have been computed, they can be output as a three-dimensional conduction velocity map in block 318. An exemplary conduction velocity map 400 is shown in FIG. 4, which includes a plurality of velocity vector icons 402. The arrowheads on vector icons 402 show the direction of the activation wavefront, while the size of vector icons 402 reflect the magnitude of the conduction velocity.

FIG. 4 further illustrates that the vector icons 402 can be arranged in a uniform grid so that adjacent icons 402 do not obscure each other. That is, rather than showing a vector icon 402 at each EP data point, which construct might lead to overlapping icons 402 and an illegible presentation, the surface of cardiac model 404 can be divided into a uniform grid having a user-determined grid size. A single vector icon 402 can be displayed in each grid square, with the magnitude and direction determined, for example, by interpolation from the conduction velocities computed at nearby EP data points. Of course, it is within the spirit and scope of the instant disclosure to display vector icons 402 at each EP data point for which a valid conduction velocity was computed.

For regular activations, such as during sinus rhythm or for regular cardiac arrhythmias, LATs can be computed relative to activation at a stable reference electrode, such as fixed reference electrode 31. Alternatively, one of the electrodes on multi-electrode catheter 13 can be selected as a reference for the computation of LATs (the selected reference electrode should itself have a validly computed LAT).

In the case of an irregular arrhythmia, however, there is often no stable activation detection that can be used as a reference for LATs. Advantageously, however, the method of computing local conduction velocities described above can be adapted to compute local conduction velocities even in the case of irregular arrhythmias. An exemplary adaptation will be described with reference to FIG. 5.

Figure 3:
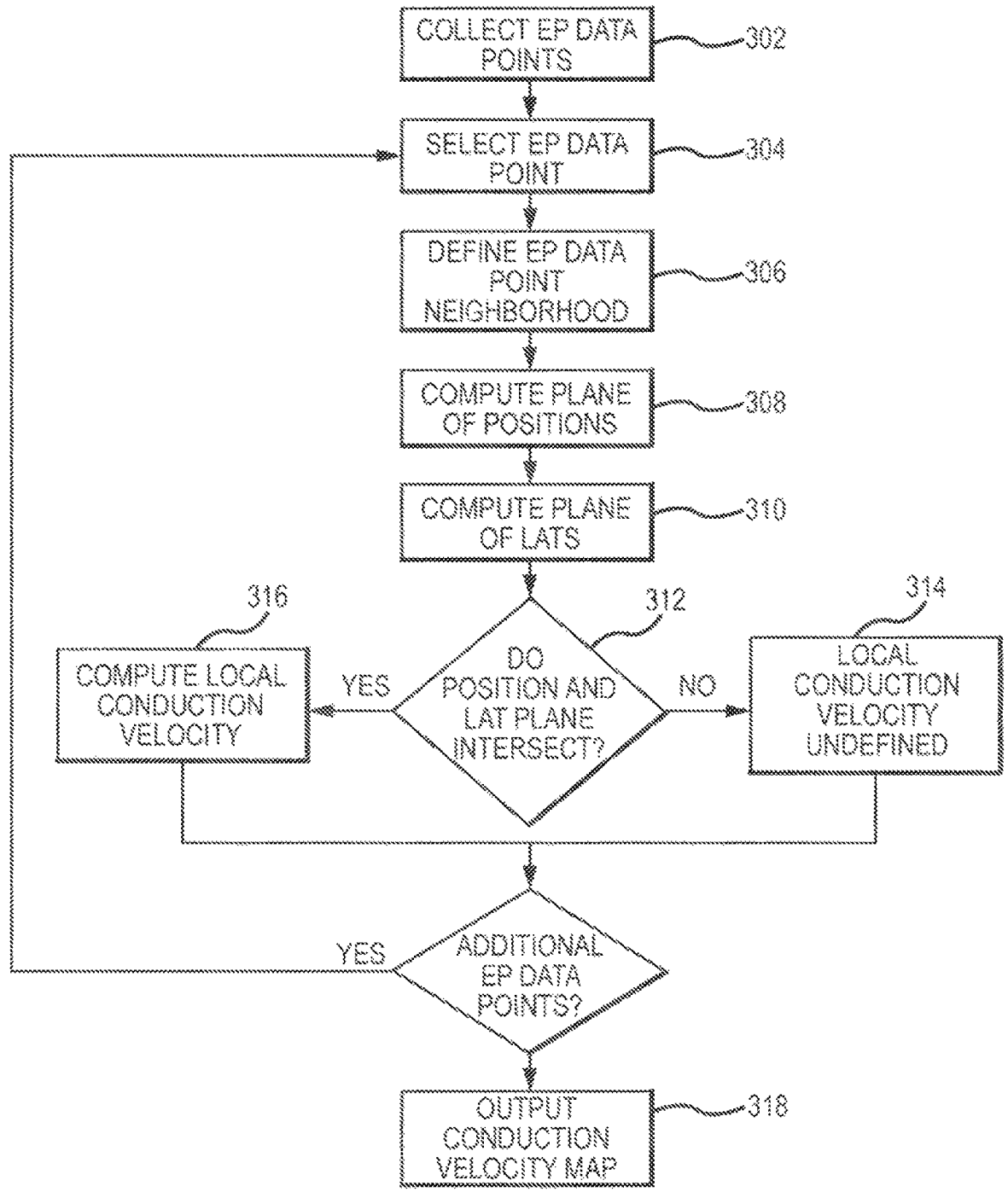
FIG. 3 is a flowchart of representative steps that can be followed to create a conduction velocity map.
Figure 5:
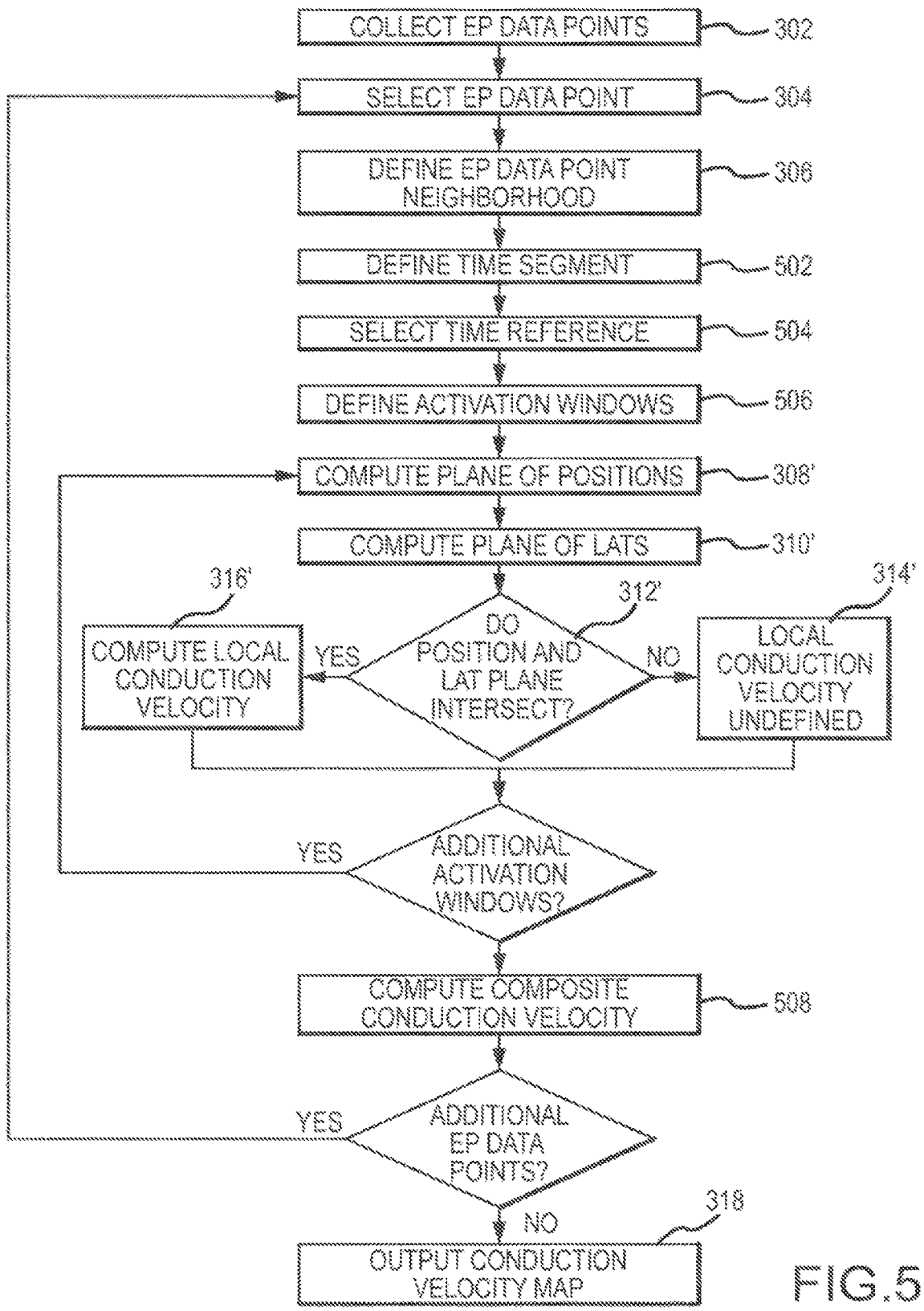
FIG. 5 is a flowchart of representative steps that can be followed to create a conduction velocity map in the case of irregular cardiac activations.

The initial steps shown in FIG. 5 are common with the initial steps shown in FIG. 3. That is, EP data points are collected in block 302, one EP data point is selected in block 304 for the computation of a local conduction velocity, and a neighborhood of EP data points is defined in block 306. The local conduction velocity at the selected EP data point, however, is computed as a composite from a plurality of conduction velocity constituents as described below.

In block 502, a time segment within which the composite conduction velocity will be computed is defined. For example, in certain aspects, the time segment is 8 seconds long, though this duration is merely exemplary and not limiting.

In block 504, one of the electrodes on multi-electrode catheter 13 is selected as an time reference for the time segment. In one embodiment, an activation detection algorithm is applied to the EP signal detected by each electrode on multi-electrode catheter 13 (that is, each intra-cardiac electrogram ("EGM") is signal processed), and the electrode having the greatest number of activations (that is, the electrode whose EGM has the smallest mean cycle length) over the time segment is selected as the time reference. Other methods of selecting a time reference are, however, contemplated.

Once a time reference is selected, the EGM for the time reference is divided into a plurality of activation windows over the time segment in block 506. Each activation window contains one activation. Each activation window can be centered at the activation contained therein, with the width of the window being user-selected.

The several activation windows are then used to compute a corresponding number of conduction velocity constituents for the selected EP data point. The computation of a conduction velocity constituent generally follows the process described above with respect to FIG. 3 (e.g., computing planes of position and LATs and then computing conduction velocity from the intersection of these planes), with each computation relative to a given activation window instead of the entire time segment. Because the steps as shown in FIG. 5 are therefore analogous to those shown in FIG. 3, the same reference numerals are used in FIG. 5 as in FIG. 3, with a "prime" designation (') used to indicate applicability to an activation window instead of a full signal.

Once conduction velocity constituents for each activation window have been computed, a composite conduction velocity for the selected EP data point during the time segment is computed in block 508. In certain embodiments, the composite conduction velocity is computed as the mathematical mean of the conduction velocity constituents $$\left(\text{i.e., } \frac{1}{N}\sum_{i=1}^{N} \overrightarrow{CV_i}\right).$$

where N is the number of activation windows for which a conduction velocity was defined (i.e., where the plane of positions and the plane of LATs intersected), and $\overrightarrow{CV_i}$ is the conduction velocity constituent within the $i^{th}$ activation window). In other embodiments, the dominant conduction velocity constituent is selected as the composite conduction velocity.

It is also contemplated that a conduction velocity consistency index can be computed from the conduction velocity constituents. The conduction velocity consistency index is a measure of the degree of consistency in the direction of the conduction velocity constituents for a given EP data point over the time segment. Thus, a high conduction velocity consistency index can be associated with a high degree of directional consistency, while a lower conduction velocity consistency index can be associated with a low degree of directional consistency (that is, a high degree of randomness in the direction of the conduction velocity constituents).

One way to compute a conduction velocity consistency index is as a ratio of the absolute magnitude of the composite conduction velocity (one suitable formula for which is described above) and the average absolute magnitude of the conduction velocity constituents (i.e., the average conduction speed, or $$\frac{1}{N}\sum_{i=1}^{N} |\overrightarrow{CV_i}|\right).$$

Another way to compute a conduction velocity consistency index is as a ratio of the absolute magnitude of the composite conduction velocity (one suitable formula for which is described above) and the absolute magnitude of the average of the conduction velocity constituents.

Still another way to compute a conduction velocity consistency index is as the average normalized dot product of the conduction velocity constituents with the composite conduction velocity.

A weighting factor, which can be a further ratio of N to the total number of activation windows, can also be included in the computation of a conduction velocity consistency index.

The conduction velocity consistency index can also be graphically displayed, such as on the exemplary conduction velocity map of FIG. 4. For example, the width of vector icon 402 can vary according to the conduction velocity consistency index.

Although several embodiments of this invention have been described above with a certain degree of particularity, those skilled in the art could make numerous alterations to the disclosed embodiments without departing from the spirit or scope of this invention.

For example, the plurality of computed local conduction velocities, and/or the resultant vector icons, can be used to determine the cardiac activation wavefront propagation trajectory.

As another example, although the conduction velocity map is described as a static map, it is contemplated that, in some embodiments, the map can be animated in order to show the propagation of the activation wavefront. Similarly, where the cardiac activation wavefront propagation trajectory is determined from the conduction velocities, that trajectory can also be displayed, highlighted, and/or animated on the map.

As yet another example, pattern recognition algorithms can be applied to identify special cardiac activation wavefront propagation patterns, such as linear, rotational, or focal patterns. Certain patterns, which may be useful for diagnosis purposes, can then be highlighted on the map.

As a still further example, a spatial continuity index can be computed from the conduction velocities of adjacent EP data points (or, in the case of a uniform grid display, adjacent grid squares). The spatial continuity index is reflective of the consistency of the direction in which the activation wavefront is propagating within a particular region of the cardiac surface, with higher values of the index generally corresponding to a higher degree of uniformity in propagation direction and lower values of the index generally corresponding to a higher degree of wave front breakups in propagation direction.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for computing local conduction velocity of a cardiac activation wavefront, comprising:
    a conduction velocity processor configured to receive as input a plurality of electrophysiology ("EP") data points, each comprising position data and local activation time ("LAT") data, collected using a multi-electrode catheter, and, for a selected EP data point:
        define a neighborhood of EP data points including the selected EP data point and at least two additional EP data points from the plurality of EP data points; and
        compute a conduction velocity for the selected EP data point using the position data of the neighborhood of EP data points and the LAT data of the neighborhood of EP data points; and
    a mapping processor configured to generate a three-dimensional graphical representation of a plurality of conduction velocities computed by the conduction velocity processor, wherein the three-dimensional graphical representation includes a plurality of conduction velocity vector icons arranged in a uniform grid over a three-dimensional model of at least a portion of a heart.

2. The system according to claim 1, wherein the conduction velocity processor is configured to compute the conduction velocity for the selected EP data point using the position data of the neighborhood of EP data points and the LAT data of the neighborhood of EP data points by:
    defining a plane of positions for the neighborhood of EP data points using the position data of the neighborhood of EP data points;
    defining a plane of LATs for the neighborhood of EP data points using the LAT data of the neighborhood of EP data points; and
    computing the conduction velocity for the selected EP data point according to an intersection between the plane of positions and the plane of LATs.

3. The system according to claim 1, wherein the LAT data are computed relative to activation at a reference electrode carried by the multi-electrode catheter.

4. The system according to claim 1, further comprising a consistency index processor configured to compute a conduction velocity consistency index for the selected EP data point, wherein the conduction velocity consistency index indicates a degree of consistency in a direction of a plurality of conduction velocity constituents for the selected EP data point.

5. The system according to claim 4, wherein the conduction velocity processor is configured to compute the plurality of conduction velocity constituents for the selected EP data point by computing a respective conduction velocity constituent for each of a plurality of activation windows of a time segment.

6. The system according to claim 4, wherein the conduction velocity consistency index comprises a ratio of an absolute magnitude of the conduction velocity and an average absolute magnitude of the conduction velocity constituents.

7. The system according to claim 4, wherein the conduction velocity consistency index comprises a ratio of an absolute magnitude of the conduction velocity and an absolute magnitude of an average of the conduction velocity constituents.

8. The system according to claim 4, wherein the conduction velocity consistency index comprises an average normalized dot product of the conduction velocity constituents and the conduction velocity.

* * * * *